United States Patent [19]
Degelmann et al.

[11] Patent Number: 5,936,081
[45] Date of Patent: Aug. 10, 1999

[54] PROCESS FOR THE HYDROGENATION OF SUGARS USING A SHELL CATALYST

[75] Inventors: Hanspeter Degelmann, Worms; Jörg Kowalczyk, Bockenheim; Markwart Kunz; Matthias Schüttenhelm, both of Worms, all of Germany

[73] Assignee: Sudzucker Aktiengesellschaft, Mannheim, Germany

[21] Appl. No.: 09/004,800

[22] Filed: Jan. 9, 1998

[30] Foreign Application Priority Data

Jan. 17, 1997 [DE] Germany ............................ 197 01 440
May 16, 1997 [DE] Germany ............................ 197 20 496

[51] Int. Cl.⁶ ..................................................... C07H 1/00
[52] U.S. Cl. ............................................................ 536/124
[58] Field of Search ................................................ 536/124

[56] References Cited

U.S. PATENT DOCUMENTS

| | | | |
|---|---|---|---|
| 3,691,100 | 9/1972 | Wright ..................................... | 252/458 |
| 4,258,222 | 3/1981 | Möhring et al. ......................... | 568/863 |
| 4,300,003 | 11/1981 | Möhring et al. ......................... | 568/863 |
| 4,413,152 | 11/1983 | Arena ...................................... | 568/863 |
| 4,608,446 | 8/1986 | Möhring et al. ......................... | 568/863 |
| 4,654,377 | 3/1987 | Möhring et al. ......................... | 521/170 |
| 5,162,517 | 11/1992 | Darsow .................................... | 536/124 |
| 5,561,217 | 10/1996 | Weyer et al. ............................. | 528/410 |

FOREIGN PATENT DOCUMENTS

| | | |
|---|---|---|
| 0 423 525 | 4/1991 | European Pat. Off. . |
| 0421882 | 4/1991 | European Pat. Off. . |
| 0773063 | 5/1997 | European Pat. Off. . |
| 0816373 | 1/1998 | European Pat. Off. . |
| 43 35 360 | 4/1995 | Germany . |
| 430576 | 6/1935 | United Kingdom . |
| 989532 | 4/1965 | United Kingdom . |
| 9314867 | 8/1993 | WIPO . |
| 9742339 | 11/1997 | WIPO . |

OTHER PUBLICATIONS

Derwent English language abstracts equivalent to DE 43 34 360.

Derwent English language abstracts equivalent to EP 0 423 525.

*Primary Examiner*—Marian C. Knode
*Assistant Examiner*—L. Eric Crane
*Attorney, Agent, or Firm*—Darby & Darby

[57] ABSTRACT

The invention relates to a process for the hydrogenation of sugars and sugar mixtures to sugar alcohols or sugar alcohol mixtures wherein the sugars or sugar mixtures are hydrogenated with hydrogen in an aqueous solution at elevated temperature and elevated pressure by using a shell catalyst comprising a mixture of a pure Raney metal and a Raney metal alloy and wherein the shell catalyst has an essentially catalytically inactive core functioning as a carrier and a catalytically active shell.

20 Claims, 2 Drawing Sheets

PROCESS FOR THE HYDROGENATION OF SUGARS USING A SHELL CATALYST

BACKGROUND OF THE INVENTION

1. Field of the Invention

The present invention relates to a process for the hydrogenation of sugars and sugar mixtures to sugar alcohols or sugar alcohol mixtures wherein the sugars or sugar mixtures are hydrogenated with hydrogen in an aqueous solution at elevated temperature and elevated pressure by using a catalyst.

2. Description of the Related Art

EP 0 152 779 B1 describes a process for manufacturing a mixture of 1-0-α-D-glocupyranosil-D-mannite (hereafter called 1,1-GPM) and 6-0-α-D-glocupyranosil-D-sorbite (hereafter called 1,6-GPS) from 6-0-α-D-glocupyranosil-D-fructose (isomaltulose, palatinose$^R$). In the described process, isomaltulose is hydrogenated continuously at elevated pressure and elevated temperature in a fixed-bed process by using catalysts taken from the eighth subgroup of the periodic system, in particular nickel, cobalt and iron. The process described above produces 1,6-GPS and 1,1-GPM with a ratio of approximately 1:1.

Another process for producing 1,6-GPS and 1,1-GPM from isomaltulose is known from DE 44 16 115 A1. Here, the catalyst described in EP 0 152 779 B1 contains additional elements from the sixth subgroup of the periodic system. This process also produces 1,6-GPS and 1,1-GPM with a ratio of about 1:1. DE 44 16 408 A1 and DE 39 34 457 A1 also describe processes for the hydrogenation of sugars, for example of glucose, xylose, lactulose or maltose. The catalysts employed in the hydrogenation reaction are carrier-free formed bodies made from elements of the eighth and sixth subgroup of the periodic system.

If stereo-isomers (epimers) can be formed by hydrogenating an educt, such as isomaltulose, then it is possible to adjust the stereo-selectivity of the reaction such that the reaction products are formed with a predetermined ratio. It is therefore desirable to develop a process for certain applications which produces reaction products with a predetermined ratio which could hitherto not be attained. It is also desirable to improve the process flow, the handling of the catalysts and the process costs of the conventional processes.

SUMMARY OF THE INVENTION

The present invention advantageously provides a process for the hydrogenation of sugars to sugar alcohols which overcomes the aforedescribed disadvantages; moreover, the products produced with the invention have a composition which was unattainable with conventional processes.

The present invention solves the technical problem by providing a process according to the independent claim. In particular, a process for the hydrogenation of sugars or sugar mixtures to sugar alcohols or sugar alcohol mixtures is provided, wherein the sugars or sugar mixtures are hydrogenated with hydrogen in an aqueous solution at elevated temperature and elevated pressure by using a shell catalyst. The shell catalyst contains a mixture of a pure Raney metal and a Raney metal alloy and has an essentially catalytically inactive core functioning as a carrier and a catalytically active shell.

The process can advantageously be used to hydrogenate xylose to xylitol, isomaltose to 1,6-GPS, glucose to sorbite, lactose to lactite, maltose to maltite, and starch hydrolysate to the corresponding sugar alcohols. In most cases, in particular with aldoses, the end product is very uniform and relatively free of by-products, isomers and decomposition products.

Most advantageously, the product produced with the process of the invention has a different composition than products obtained with conventional processes, in particular if different stereo-isomers are produced from an educt, for example ketoses, in a hydrogenation reaction.

In a preferred embodiment, the process of the invention produces a somewhat larger fraction of sorbite epimer and a somewhat smaller fraction of mannite epimer, if the ketoses are fructose or fructose derivatives.

In another preferred embodiment, isomaltulose is hydrogenated. The composition of the reaction product is here different from the composition obtained with a conventional process, which yields about 50 wt.-% 1,1-GPM and 50 wt.-% 1,6-GPS. In a preferred embodiment, the reaction product has a smaller 1,1-GPM (mannite epimer) fraction and a larger 1,6-GPS (sorbite epimer) fraction.

The process of the invention can advantageously also be used for hydrogenating sugar mixtures, such as the mixture of isomaltulose and trehalulose described in EP 62 55 78 B1, and possibly also glucose, fructose and other oligo-saccharides. In a preferred embodiment, the hydrogenation produces a larger sorbite epimer fraction (1,1-GPS, 1,6-GPS) and a smaller mannite epimer fraction (1,1-GPM) in the product. In the same preferred embodiment, hydrogenation of other sugars listed below produces a comparatively larger sorbite epimer fraction and a smaller mannite epimer fraction in the product. In another preferred embodiment, the hydrogenation of fructose produces a larger sorbite fraction (sorbite epimer), whereas the hydrogenation of lactulose in still another preferred embodiment produces a slightly lactite concentration (3-0-b-D-galactopyranosyl-D-sorbite) (sorbite epimer).

In yet another preferred embodiment, hydrogenation of other sugars listed below produces a larger mannite epimer fraction and a smaller sorbite epimer fraction in the product in comparison to the conventional catalysts. The invention can therefore advantageous be used to hydrogenate trehalulose to 1,1-GPM and 1-0-a-D-glocupyranosil-D-sorbite (1,1-GPS) and maltulose to 3-0-a-D-glucopyranosil-D-mannite as well as 4-0-a-D-glucopyranosil-D-sorbite (maltite). In the preferred embodiment, especially trehalulose produces a comparatively larger 1,1-GPM fraction, whereas maltulose produces a greater fraction of the similar mannite epimer (1,3-GPM).

Those sugar alcohol stereo isomers are referred to as mannite and sorbite epimers which are produced during hydrogenation of the prochiral carbonyl carbon atom of the ketose and fructose, respectively, or the glucopyranosil-substituted fructose or ketose (isomaltulose, trehalulose, etc.). In the context of the present invention, a mannite epimer is an epimer which has the polyol chain of the, if necessary glucopyranosil-substituted, D-mannose. A sorbite epimer is an epimer which has the polyol chain of the, if necessary glucopyranosil-substituted, D-glucose.

The shell catalyst used with the invention contains a Raney metal alloy and a pure Raney metal, with the Raney metal providing the binder for the Raney metal alloy. The catalyst is prepared by homogenizing and forming a Raney metal alloy with a pure Raney metal, for example in powder form, possibly together with lubricants, deformeable additives, plastifiers and pore forming materials, wherein the formed bodies are formed by extrusion or pressing. The formed bodies can be dried between 80° C. and 120° C. and subsequently calcined at temperatures below 850° C., preferably between 500° C. and 700° C. The catalytic precursors so formed have a homogeneous structure and are subsequently treated and activated with a sodium hydroxide solution, such as a 20% sodium hydroxide solution at a temperature of 80° C., for two hours. The activation step creates a 0.05 to 1.0 mm thick lixiviated shell forming the active catalyst. The core of the catalyst is not lixiviated and is therefore substantially catalytically inactive, forming essentially the carrier of the active shell.

In a particularly preferred embodiment, the Raney metals are nickel, cobalt, copper or iron. In still another preferred embodiment, a Raney metal alloy is preferred which is prepared from a Raney metal, for example nickel, cobalt, copper or zinc with a lixiviatable alloy component, such as like aluminum, tin or silicon. The weight ratio of the Raney metal to the lixiviatable alloy component can be between 30:70 and 70:30. The weight ratio of the Raney metal alloy to the pure Raney metal can be between 100:20 and 100:0.5. The particle size of the pure Raney metal, i.e. the binder, should be smaller than the particle size of the metal alloy. In a particularly preferred embodiment, 99 wt.-% of the catalyst precursor represent the pure Raney metal and the Raney metal alloy.

The composition and the preparation of the catalyst used with the present invention are described in DE 43 35 360 A1 to which reference is made with respect to the composition and the preparation of the catalyst used in the present invention, and which is incorporated herein by reference.

In still another preferred embodiment, the catalyst has a pore volume of up to 0.5 cm$^3$/g, more particularly between about 0.03 and about 0.06 cm$^3$/g. The pore volume can be determined by measuring the water absorption after the catalyst has been deactivated with hydrogen peroxide. According to the invention, the catalyst has preferably a density of between about 1.3 and about 5.5 g/cm$^3$.

In yet another preferred embodiment, the catalyst has a crushing strength in excess of about 200 N, preferably in excess of about 300 N.

According to the invention, the catalysts have a BET surface of between about 1 and about 50 m$^2$/g, preferably between about 1 and about 25 m$^2$/g. The BET surface can be determined with the Brunauer, Emmet and Teller method (DIN 66132).

The catalysts used with the present invention can be doped, i.e. they can contain in addition to the Raney metals and Raney metal alloys—other metals in concentrations of up to 20 wt.-%, preferably 15 wt.-%, relative to the formed body. These metals include, for example, chromium, cobalt, titanium, platinum, iron, tantalum, molybdenum or ruthenium.

The catalysts used with the present invention can be prepared by an extrusion process. The catalysts are preferably prepared by compressing powder under high pressure, wherein graphite and/or adhesive in quantities of less than 1 wt.-%, referenced to the weight of the catalyst, can be added, if necessary, to improve the adhesion of the particles. The catalysts can contain lubricants, deformeable additives, plastifiers, etc., which are added to aid in the formation of the formed bodies. The catalysts can have the form of spheres, tablets, granulates, rods, with or without bores. The catalysts can, of course, also be in powder form when used, for example, in a suspension process.

The educt used in the process of the invention is glucose, fructose, xylose, lactose, maltose, isomaltose, lactulose, trehalulose, maltulose, isomaltulose, leucrose, starch hydrolysate or mixtures thereof. The sugars can be in liquid or in crystalline form. According to a particularly preferred embodiment of the invention, the educt is dissolved in demineralized water, with the solution adjusted to about 10 to about 70 wt.-%, preferably about 15 to about 50 wt.-%, most preferably about 40 wt.-% (referenced to dry solid). The pH value is preferably between 3.0 and 12.0. The pH value can be adjusted, for example, by adding water-soluble basic compounds, such as alkali carbonates or ammonia in aqueous solution, or by adding acidic compounds, such as saccharic acids, sorbic acid or citric acid.

In the process of the invention, pure hydrogen which is precompressed to about 50 to about 450 bar, preferably to about 150 to about 300 bar, is used for hydrogenation. The stoichiometric ratio of the saccharide which is to be reduced, to hydrogen is preferably 1 to above 3, most preferably 1 to 7. Preferably, the hydrogenation can be carried out continuously in a fixed-bed process or semi-continuously, using a conventional parallel flow or a counterflow process. According to the invention, the hydrogenation can also be carried out discontinuously with a suspension process or with a process where the catalyst is held in a catalyst basket.

With the suspension process which is operated either continuously or discontinuously, the catalyst can be in form of a powder or of a pulverized formed body.

The process of the invention is preferably carried out in a hydrogenation reactor in the form of a high-pressure steel tube, wherein the hydrogenation reactor is filled either partially or entirely with the catalyst which is either carrier-free or attached to a carrier. The catalyst can also be placed in a catalyst basket. It is understood by those skilled in the art that hydrogenation reactors can also be used which are constructed, for example, from a variety of individual reactors. In a particularly preferred embodiment of the invention, the hydrogenation reactor includes stirrers for bringing the educts and the hydrogenation gas into closer contact with each other.

The hydrogenation is preferably carried out at temperatures between about 60° C. and about 150° C., preferably between about 70° C. and about 120° C.

With the process of the invention, sugar alcohols or sugar alcohol mixtures with a purity of better than 99 wt.-%, referenced to the solid mass, can be obtained. The fraction of unreacted sugars or sugar mixtures can be reduced to 0.2 wt.-% or less.

The composition of products which contain stereoisomers can be positively controlled by hydrogenating the educt under a predetermined stoichiometric ratio of educt to hydrogen. In a preferred embodiment, an increase in the stoichiometric hydrogen/educt ratio lowers the mannite/sorbite epimer ratio, i.e. more sorbite epimer is generated, and vice versa. The quantity of hydrogen supplied or the educt flow determines the hydrogen/educt ratio.

Other objects and features of the present invention will become apparent from the following detailed description considered in conjunction with the accompanying drawings. It is to be understood, however, that the drawings are intended solely for purposes of illustration and not as a definition of the limits of the invention, for which reference should be made to the appended claims.

BRIEF DESCRIPTION OF THE DRAWINGS

The invention will now be described in greater detail with reference to the appended drawing and the related embodiments. In the drawing is shown in.

EXAMPLES AND DETAILED DESCRIPTION OF THE PRESENTLY PREFERRED EMBODIMENTS

Example 1

Figure 1:
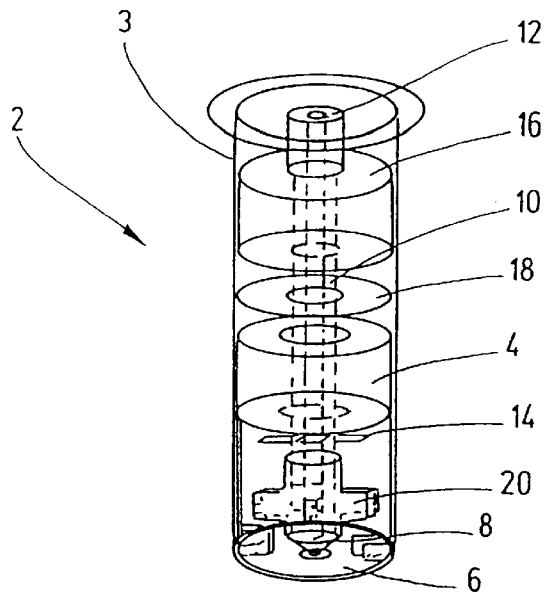
FIG. 1 a schematic illustration of a hydrogenation reactor used in accordance with the invention.

Hydrogenation of isomaltulose with the process of the invention and with a shell Raney nickel catalyst:

Isomaltulose was hydrogenated in a hydrogenation reactor 2 with an inner volume of 750 ml using the discontinuous fixed-bed process. A catalyst basket 4 with an inner volume of 133.9 cm$^3$ is located inside a stainless steel tube in the hydrogenation reactor 2.

The catalyst basket 4 contains 227.4 g (wet) catalyst. The catalyst is used in the form of 4 mm tablets and is prepared from a nickel/aluminum alloy (Ni:Al equals 53:47 wt.-%) and pure nickel as binder with a ratio of 100:15 by weight.

2.1 wt.-% wax powder, referenced to the total weight of the catalyst, was added as pore former. This mixture was then homogenized and temporarily dried and subsequently calcined at 700° C. for two hours. The crush strength after the calcination step was 280 N. The shell thickness after activation with 20% soda lye at 80° C. for two hours was 0.3 mm and the crush strength >300 N. The activated catalysts were stored under water and then used in the experiments of examples 1 to 12.

The centering disc 6 of the hydrogenation reactor 2 which is located near the bottom of the reactor 2, includes a lower shaft bearing 8. The lower shaft bearing 8 and the upper shaft bearing 12 support a stainless steel stirrer shaft 10 which carries stirring paddles 14. The stirrer shaft 10 is driven electro-magnetically by the stirrer magnet 16. In FIG. 1, there are also illustrated flow interrupters 18 and a gas distribution paddle 20.

500 ml aqueous educt solution, in the present example isomaltulose solution (30 wt.-% dry solid), are introduced into the hydrogenation reactor 2. Hydrogen under a pressure of 150 bar is introduced through the gas distribution paddle 20, while the stirrer 10 rotates at 600 RPM and a temperature of 70° C. is maintained. Samples from the reagent solution are withdrawn at the beginning of the reaction and after 2, 3, 4, 5, 6 and 22 hours and tested for isomaltulose, 1,1-GPM, 1,6-GPS, mannite, sorbite and saccharite residue.

Figure 2:
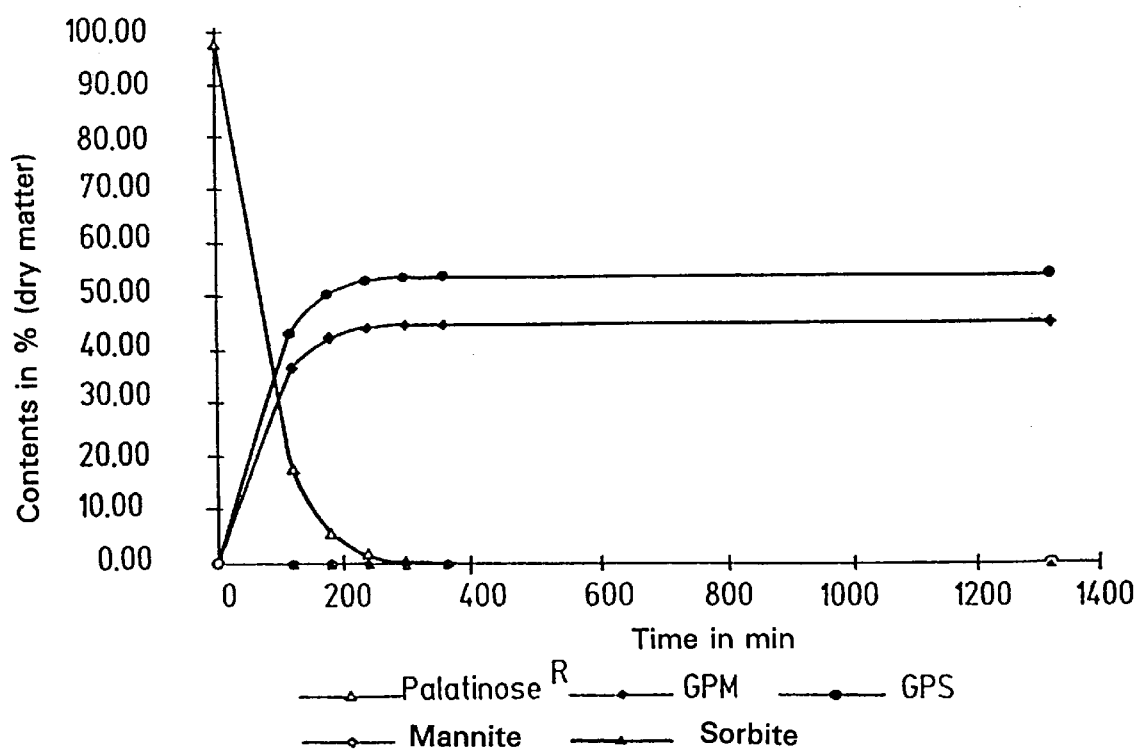
FIG. 2 a graphic representation of the product formation according to FIG. 1 as a function of time.

The results are shown in Table 1 and graphed in FIG. 2.

TABLE 1

| Sample designation | Fructose % | Glucose % | isomaltulose % | trehalulose % | isomaltose % | Residue % |
|---|---|---|---|---|---|---|
| Starting solution | 0.1 | 0.0 | 98.3 | 1.1 | 0.3 | 0.2 |

| Duration of the experiment in min. | Isomaltulose % | 1,1-GPM | 1,6-GPS | Mannite | Sorbite | Residue |
|---|---|---|---|---|---|---|
| 0 | 98.30 | 0.00 | 0.00 | 0.00 | 0.00 | 1.70 |
| 120 | 18.05 | 36.82 | 43.74 | 0.01 | 0.12 | 1.26 |
| 180 | 5.46 | 42.59 | 50.76 | 0.06 | 0.08 | 1.05 |
| 240 | 1.33 | 44.41 | 53.30 | 0.04 | 0.11 | 0.81 |
| 300 | 0.37 | 44.98 | 53.83 | 0.03 | 0.10 | 0.69 |
| 360 | 0.11 | 45.11 | 53.91 | 0.06 | 0.08 | 0.73 |
| 1320 | 0.05 | 45.22 | 54.02 | 0.05 | 0.09 | 0.57 |

Hydrogenation of isomaltulose (=palatinose$^R$) produces a product with a composition which is different from the expected 1:1 ratio of 1,1-GPM to 1,6-GPS. The process of the invention produces a larger fraction of 1,6-GPS and a smaller fraction of 1,1-GPM in the end product (see also FIG. 2).

Example 2

Hydrogenation of isomaltulose

The conditions and the apparatus for the process are identical to those described in Example 1. However, only one sample was drawn after 22 hours. The educt used here has the composition shown in Table 2 (in the following, % values are given in wt.-%, unless indicated otherwise):

TABLE 2

| No. | Educt | Contents |
|---|---|---|
| 1 | Isomaltulose | 98.50% as dry solid |
| 2 | Trehalulose | 1.13% as dry solid |
| 3 | Isomaltose | 0.23% as dry solid |
| 4 | Isomelezitose | 0.08% as dry solid |
| 5 | Saccharide residue | 0.06% as dry solid |

It is evident from Table 3 that the product produced with the process of the invention has a different composition than products obtained with an otherwise identical process which uses a reference catalyst. A carrier-free Raney nickel catalyst which was prepared by compressing activated nickel powder into tablets, was used for the reference process. The tablets are cylindrical with a height of 5 mm and a diameter of 5 mm and have a crush strength of 147 N and an interior surface of 33 m$^2$/g.

TABLE 3

| No. | Product | Reference process | Invention |
|---|---|---|---|
| 1 | 1,1-GPM | 49.09% as dry solid | 42.90% as dry solid |
| 2 | 1,6-GPS | 49.45% as dry solid | 56.33% as dry solid |
| 3 | GPI | 0.33% as dry solid | 0.05% as dry solid |
| 4 | Mannite | 0.05% as dry solid | 0.04% as dry solid |
| 5 | Sorbite | 0.11% as dry solid | 0.10% as dry solid |
| 6 | hydrogenated and unhydrogenated saccharide residues | 0.97% as dry solid | 0.58% as dry solid |

(GPI: glucopyranosyl-Idite)

The reference process produces 1,1-GPM and 1,6-GPS with a 1:1 ratio, whereas the process of the invention produces a greater 1,1-GPM fraction and a smaller 1,6-GPS fraction in the product. Moreover, the products of the invention contain less decomposition products and by products than products produced with the reference process.

Example 3

Hydrogenation of a mixture of isomaltulose and trehalulose (known from EP 0 625 578 B1):

The process flow and the apparatus for the process are identical to those described in Example 1. The reference method uses a catalyst identical to the catalyst of Example 2.

The educt in this example is a sugar mixture with the composition shown in Table 4:

TABLE 4

| No. | Educt | Contents |
| --- | --- | --- |
| 1 | Fructose | 3.64% as dry solid |
| 2 | Glucose | 2.50% as dry solid |
| 3 | Saccharose | 0.06% as dry solid |
| 4 | Isomaltulose | 84.02% as dry solid |
| 5 | Trehalulose | 7.64% as dry solid |
| 6 | Isomaltose | 1.39% as dry solid |
| 7 | Isomelezitose | 0.38% as dry solid |
| 8 | Saccharide residue | 0.43% as dry solid |

Hydrogenation with the process of the invention and with the reference process the following result:

TABLE 5

| No. | Product | Reference process | Invention |
| --- | --- | --- | --- |
| 1 | 1,1-GPM | 46.52% as dry solid | 41.16% as dry solid |
| 2 | 1,6-GPS + 1,1-GPS | 46.41% as dry solid | 50.97% as dry solid |
| 3 | Mannite | 1.60% as dry solid | 1.62% as dry solid |
| 4 | Sorbite | 3.85% as dry solid | 4.44% as dry solid |
| 5 | hydrogenate and unhydrogenated saccharide residues | 1.62% as dry solid | 1.81% as dry solid |

The reference process produces 1,1-GPM and 1.1-GPS/1,6-GPS with a ratio of about 1:1, whereas the process of the invention produces a greater 1.1-GPS/1,6-GPS fraction and a smaller 1,1-GPM fraction in the product.

Example 4

Hydrogenation of fructose

The process flow and the apparatus for the process are identical to those described in Example 1. The reference method uses a catalyst identical to the catalyst of Example 2.

Hydrogenation of fructose (100 wt.-%, 0.52 wt.-%, referenced to dry solid) with the process of the invention and with the reference process gives the following result:

TABLE 6

| No. | Product | Reference process | Invention |
| --- | --- | --- | --- |
| 1 | Mannite | 48.55% as dry solid | 47.62% as dry solid |
| 2 | Sorbite | 48.55% as dry solid | 52.57% as dry solid |
| 3 | Idite | 0.81% as dry solid | 0.17% as dry solid |
| 4 | hydrogenated and unhydrogenated saccharide residues | 2.09% as dry solid | 0.64% as dry solid |

The ratio of mannite to sorbite in the reference process is 1:1, whereas the process of the invention increases the sorbite fraction and decreases the mannite fraction in the process.

Example 5

Hydrogenation of glucose

The process flow and the apparatus for the process are identical to those described in Example 1. The reference method uses a catalyst identical to the catalyst of Example 2.

Hydrogenation of glucose (99.91 wt.-% glucose, 0.09 wt.-% saccharide residue, referenced to dry solid) with the process of the invention and with the reference process gives the following result:

TABLE 7

| No. | Product | Reference process | Invention |
| --- | --- | --- | --- |
| 1 | Sorbite | 97.46.55% as dry solid | 99.45% as dry solid |
| 2 | Mannite | 0.91% as dry solid | 0.13% as dry solid |
| 3 | Idite | 0.03% as dry solid | 0.03% as dry solid |
| 4 | hydrogenated and unhydrogenated saccharide residues | 1.60% as dry solid | 0.39% as dry solid |

The process of the invention hydrogenates glucose to sorbite more selectively than the reference process. The mannite fraction and the concentration of other by-products in the product are reduced significantly with the invention.

Example 6

Hydrogenation of lactulose

The process flow and the apparatus for the process are identical to those described in Example 1. The reference method uses a catalyst identical to the catalyst of Example 2.

Hydrogenation of lactulose (98.96 wt.-% lactulose, 0.47 wt.-% saccharose, 0.29 wt.-% glucose and 0.27 wt.-% unknown saccharides, referenced to dry solid) with the process of the invention and with a conventional process gives the following result:

TABLE 8

| No. | Product | Reference process | Invention |
| --- | --- | --- | --- |
| 1 | β-1,3-GalPM | 46.38% as dry solid | 45.17% as dry solid |
| 2 | Lactite (β-1,4-GalPS) | 51.62% as dry solid | 52.15% as dry solid |
| 3 | Galactite | 0.93% as dry solid | 0.86% as dry solid |
| 4 | Sorbite | 0.04% as dry solid | 0.03% as dry solid |
| 5 | hydrogenated and unhydrogenated saccharide residues | 1.03% as dry solid | 1.79% as dry solid |

The process of the invention produces a comparatively slightly greater 1,4-GalPS fraction and a comparatively smaller 1,3-GalPM fraction in the product.

Example 7

Hydrogenation of trehalulose

The process flow and the apparatus for the process are identical to those described in Example 1. The reference method uses a catalyst identical to the catalyst of Example 2.

The educt which was used, is a sugar mixture with the composition shown in Table 9:

TABLE 9

| No. | Educt | Contents |
| --- | --- | --- |
| 1 | trehalulose | 92.55% as dry solid |
| 2 | Fructose | 0.18% as dry solid |
| 3 | Glucose | 1.72% as dry solid |
| 4 | Saccharose | 0.08% as dry solid |
| 5 | Isomaltulose | 2.79% as dry solid |
| 6 | Unknown saccharides | 2.68% as dry solid |

Hydrogenation with the process of the invention and with the reference process gives the following result:

TABLE 10

| No. | Product | Reference process | Invention |
| --- | --- | --- | --- |
| 1 | 1,1-GPM | 53.29% as dry solid | 56.74% as dry solid |
| 2 | 1,1-GPS, 1,6-GPS | 41.10% as dry solid | 38.45% as dry solid |
| 3 | Mannite | 0.02% as dry solid | 0.03% as dry sohd |
| 4 | Sorbite | 1.02% as dry solid | 1.23% as dry solid |
| 5 | hydrogenated and unhydrogenated saccharide residues | 4.57% as dry solid | 3.55% as dry solid |

The process of the invention produces a larger 1,1-GPM fraction in the product than the conventional process. The 1,1-GPS fraction is reduced accordingly. The 1,6-GPS is produced by the isomaltulose residues contained in the educt.

Example 8
Hydrogenation of maltulose

The process flow and the apparatus for the process are identical to those described in Example 1. The reference method uses a catalyst identical to the catalyst of Example 2.

The composition of the educt was as follows:

TABLE 11

| No. | Educt | Contents |
| --- | --- | --- |
| 1 | Maltulose | 83.43% as dry solid |
| 2 | Fructose | 5.74% as dry solid |
| 3 | Glucose | 3.87% as dry solid |
| 4 | Saccharide residue | 6.96% as dry solid |

Hydrogenation with the process of the invention and with the reference process gives the following result:

TABLE 12

| No. | Product | Reference process | Invention |
| --- | --- | --- | --- |
| 1 | 1,3-GPM | 37.29% as dry solid | 44.31% as dry solid |
| 2 | 1,4-GPS (Maltite) | 41.49% as dry solid | 43.95% as dry solid |
| 3 | Sorbite | 7.36% as dry solid | 7.57% as dry solid |
| 4 | Mannite | 5.44% as dry solid | 2.93% as dry solid |
| 5 | hydrogenated and unhydrogenated saccharide residues | 7.97% as dry solid | 1.25% as dry solid |

The process of the invention improves the total yield of 1,3-GPM and 1,4-GPS as well as a higher concentration of the mannite epimers than of the sorbite epimers in the product.

Example 9
Hydrogenation of invert sugar

The process flow and the apparatus for the process are identical to those described in Example 1. The reference method uses a catalyst identical to the catalyst of Example 2.

The educt used represents a sugar mixture with the composition shown in Table 13:

TABLE 13

| No. | Educt | Contents |
| --- | --- | --- |
| 1 | Fructose | 47.30% as dry solid |
| 2 | Glucose | 49.62% as dry solid |
| 3 | Saccharose | 1.11% as dry solid |
| 4 | Saccharide residue | 1.97% as dry solid |

Hydrogenation with the process of the invention and with the reference process gives the following result:

TABLE 14

| No. | Product | Reference process | Invention |
| --- | --- | --- | --- |
| 1 | Mannite | 21.93% as dry solid | 20.49% as dry solid |
| 2 | Sorbite | 74.27% as dry solid | 75.84% as dry solid |
| 5 | hydrogenated and unhydrogenated saccharide residues | 3.80% as dry solid | 3.67% as dry solid |

The process of the invention produces a slightly higher sorbite fraction and a comparatively slightly lower mannite fraction in the product.

Example 10

Hydrogenation of sugars with powder catalysts (slurry process, discontinuous process):

(1) Autoclave system and experimental parameters:

| | |
| --- | --- |
| 750 ml laboratory autoclave with inductively operated stirrer | |
| Reaction temperature | 70° C. |
| Hydrogen pressure | 150 bar |
| Stirrer RPM | 600 rpm |
| Sugar solution | 500 ml with 30% dry solid |
| Catalyst quantity | ca. 25 g (wet) |
| Reaction time | 22 h |

(2) Assay

The reaction solution (500 ml, 30% dry solid) is introduced into the temperature-stabilized autoclave of FIG. 1; however, the basket is omitted and the stirrer is modified. Subsequently, 25 g powdered catalyst (the catalyst has the same composition as in Example 1) is added, whereafter (not before) the stirrer shaft is inserted. The system is then rendered inert by purging 3 times with nitrogen, whereafter hydrogenation is carried out at 150 bar and a reaction temperature of 70° C. After 22 hours, the system is cooled down to room temperature and depressurized. After the system is purged with nitrogen, the product solution is withdrawn and the catalyst filtered out.

Example 11
Hydrogenation of a mixture of isomaltulose and trehalulose (known from EP 625 578 B1)

The process flow and the apparatus for the process are identical to those described in Example 10.

The educt is s sugar mixture with the composition shown in Table 16:

TABLE 15

| No. | Educt | Contents |
| --- | --- | --- |
| 1 | Fructose | 3.73% as dry solid |
| 2 | Glucose | 2.84% as dry solid |
| 3 | Isomaltulose | 84.43% as dry solid |
| 4 | Trehalulose | 7.32% as dry solid |

TABLE 15-continued

| No. | Educt | Contents |
|-----|-------|----------|
| 5 | Isomaltose | 0.93% as dry solid |
| 6 | Isomelezitose | 0.47% as dry solid |
| 7 | Residue | 0.28% as dry solid |

The hydrogenation according to the present invention gives the following result:

TABLE 16

| No. | Product | Invention |
|-----|---------|-----------|
| 1 | 1,1-GPM | 44.66% as dry solid |
| 2 | 1,1-GPS + 1,6-GPS | 47.46% as dry solid |
| 3 | Mannite | 1.83% as dry solid |
| 4 | Sorbite | 4.32% as dry solid |
| 5 | hydrogenated and unhydrogenated saccharide residues | 1.73% as dry solid |

The product contains more 1,1-GPS/1,6-GPS and less 1,1-GPM than expected (a 1:1 ratio of 1,1-GPS/1,6-GPS to 1,1-GPM was expected).

Example 12
Hydrogenation of isomaltulose under different stoichiometric hydrogen/isomaltulose ratios The process flow and the apparatus for the process are identical to those described in Example 1. The educt is also identical to the educt of Example 1.

Figure 3:
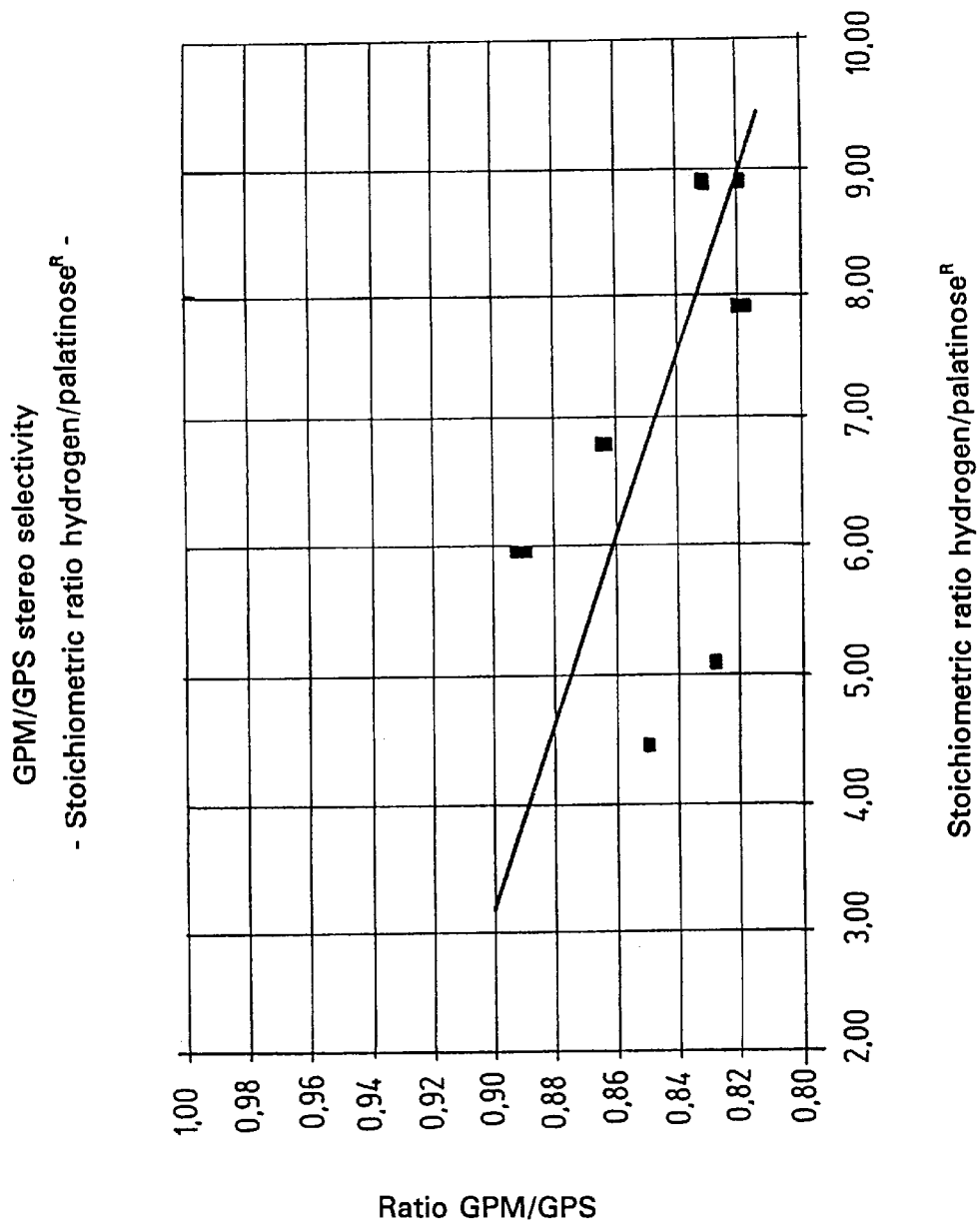
FIG. 3 a graphic representation of the functional dependence of the 1,1-GPM/1,6-GPS ratio on the stoichiometric ratio hydrogen/isomaltulose (palatinose$^R$).

In the present example, the stoichiometric ratio of hydrogen to educt, i.e. the isomaltulose, was varied, so that—as shown in FIG. 3—the ratio (wt.-%/wt.-%, referenced to the dry solid of the resulting product mixture) of the products 1,1-GPM to 1,6-GPS could be regulateded. A decrease in the stoichiometric hydrogen/isomaltulose ratio led to an increase in the 1,1-GPM/1,6-GPS ratio. With the present invention, the composition of the product mixture containing the stereo-isomer products can be regulated by varying the stoichiometric hydrogen/isomaltulose ratio, for example by adjusting the isomaltulose flow during hydrogenation.

Example 13
Hydrogenation of various sugars or sugar mixtures with the process of the invention and with a shell Raney copper catalyst The process flow and the apparatus for the process are, if not indicated otherwise, identical to those described in Example 1. The catalyst used in this example had the following composition:

The catalyst is made from a copper/aluminum alloy (Cu:Al equal to 50:50 wt.-%) and pure copper as binder with a ratio by weight of 100:15. The catalyst is in form of 4 mm tablets. The catalyst basket contains 224.05 g catalyst (wet).

2.1 wt.-% wax powder, referenced to the total weight of the catalyst, was added as pore former (referenced to the total weight of the catalyst). This mixture was then homogenized and temporarily dried and subsequently calcined at 500° C. for six hours. The crush strength after the calcination step was >300 N. The shell thickness after activation with 20% soda lye at 80° C. for two hours was 0.3 mm and the crush strength >300 N. The activated catalysts were stored under water.

Table 17 shows the results of hydrogenating a mixture of essentially isomaltulose and trehalulose (known from, for example, EP 0 625 578 B1), as well as of fructose, invert sugar and isomaltulose with the process of the invention using a Raney copper catalyst. The composition of the educt and of the product in Table 17 is given in wt.-%.

The mixture which is obtained by hydrogenating a mixture of essentially isomaltulose and trehalulose, contains—in comparison to conventional processes—a large quantity of 1,1-GPM and only a small quantity of 1,1-GPS and 1,6-GPS. The conventional reference catalyst was described above in Example 2.

When fructose is hydrogenated, the resulting product mixture contains—in comparison to conventional processes—a rather large mannite fraction and a comparatively small sorbite fraction.

When invert sugar is hydrogenated, the resulting product mixture contains—in comparison to conventional processes—a larger mannite fraction and a smaller sorbite fraction.

When isomaltulose is hydrogenated, the resulting product mixture contains—in comparison to conventional processes—a larger 1,1-GPM fraction and a smaller 1,6-GPS and 1,1-GPS fraction.

TABLE 17

| Component | Isomaltulose and trehalulose | | Fructose | | Invert sugar | | Isomaltulose | |
|-----------|------------------|---------------|---------------|---------------|---------------|---------------|---------------|---------------|
| | Educt wt. % | Product wt. % | Educt wt. % | Product wt. % | Educt wt. % | Product wt. % | Educt wt. % | Product wt. % |
| Fructose | 3.66 | | 10.00 | 1.60 | 46.93 | 0.19 | 0.12 | |
| Glucose | 2.61 | | | 0.12 | 49.36 | 0.58 | | |
| Saccharose | 0.00 | | | | 1.71 | 0.11 | | |
| Isomaltulose | 84.09 | 0.30 | | | | 0.20 | 98.92 | 0.65 |
| Isomelezitose | 0.37 | 0.28 | | | | | | 0.04 |
| Trehalulose | 8.19 | 5.61 | | | | 0.09 | 0.63 | 0.31 |
| Isomaltose | 0.88 | | | | | 0.18 | 0.20 | |
| 1,1-GPM | | 60.79 | | | | | | 64.0 |
| 1,6-GPS + 1,1-GPS | | 25.18 | | | | | | 34.14 |
| Erythrite | | 0.04 | | | | | | |
| Glycerin | | 0.06 | | | | | | |
| Mannite | | 2.56 | | 61.59 | | 31.59 | | 0.05 |
| Sorbite | | 3.93 | | 36.18 | | 65.74 | | 0.08 |
| Idite | | | | | | 0.04 | | |
| Galactite | | | | | | | | |

TABLE 17-continued

| Component | Isomaltulose and trehalulose | | Fructose | | Invert sugar | | Isomaltulose | |
|---|---|---|---|---|---|---|---|---|
| | Educt wt. % | Product wt. % | Educt wt. % | Product wt. % | Educt wt. % | Product wt. % | Educt wt. % | Product wt. % |
| Unknown (hydrogenated and unhydrogenated) | 0.20 | 1.25 | | 0.52 | 1.53 | 1.76 | 0.13 | 0.53 |
| Sum | 100.00 | 100.00 | 100.00 | 100.00 | 100.00 | 100.00 | 100.00 | 100.00 |
| Purity Product | | 86.23 | | 98.78 | | 98.19 | | 98.99 |
| Purity Educt | 84.09 | | 100.00 | | 96.29 | | 98.92 | |
| Hydrogenation temperature | 90° C. | | 90° C. | | 120° C. | | 70° C. | |
| Reaction time | 22 h | | 22 h | | 22 h | | 22 h | |

Thus, while there have been shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Substitutions of elements from one described embodiment to another are also fully intended and contemplated. It is also to be understood that the drawings are not necessarily drawn to scale but that they are merely conceptual in nature. It is the intention, therefore, to be limited only as indicated by the scope of the claims appended hereto.

What is claimed is:

1. A method for the hydrogenation of a sugar to a sugar alcohol, said method comprising:
    a) preparing a shell catalyst said preparation comprising:
        (i) homogenizing and forming a Raney metal alloy with a pure Raney metal into a formed body;
        (ii) drying said formed body;
        (iii) calcining said formed body below about 850° C. to produce a catalytic precursor; and
        (iv) exposing said catalytic precursor to a sodium hydroxide solution to produce a catalytically active shell having a catalytically inactive core;
    b) contacting said sugar with hydrogen in an aqueous solution in the presence of said shell catalyst prepared in step a).

2. The method as defined in claim 1, wherein the pure Raney metal consists of at least one metal selected from the group consisting of nickel, cobalt, copper, and iron and the Raney-metal-alloy is prepared by combining one metal selected from the group consisting of nickel, cobalt, copper, and iron with at least one metal from the group consisting of aluminum, tin, and silicon.

3. A method as defined in claim 1, wherein the homogenizing and forming step (i) further comprises at least one additional constituent selected from the group consisting of lubricants, deformable additives, plastifiers and pore forming materials.

4. A method as defined in claim 1, wherein said contacting step b) is carried out with a fixed-bed process.

5. The method as defined in claim 1, wherein said shell catalyst has a crushing strength in excess of about 200 N.

6. The method as defined in claim 5, wherein said shell catalyst has a crushing strength in excess of about 300 N.

7. The method as defined in claim 2, wherein said catalytically active shell has a thickness of between about 0.05 and about 1.0 mm.

8. The method as defined in claim 1, said shell catalyst has a pore volume between about 0.03 and about 0.06 cm$^3$/g.

9. The method as defined in claim 1, wherein said catalyst has a BET surface between about 1 and about 50 m$^2$/g.

10. The method as defined in claim 1, wherein said sugar is selected from the group consisting of glucose, isomaltose, maltose, lactose, starch hydrolysate, fructose, xylose, lactulose, trehalulose, maltulose, isomaltulose, leucrose, a fructo-oligosaccharide, and mixtures of any of the foregoing.

11. The method as defined in claim 1, wherein said contacting step b) is selected from the group consisting of continuous, semi-continuous and discontinuous.

12. A method as defined in claim 1, wherein said catalytic precursor is formed by pressing.

13. The method as defined in claim 1, wherein the contacting step b) is carried out at a hydrogen pressure between about 50 and about 450 bar.

14. The method as defined in claim 13, wherein the contacting step b) is further carried out at a temperature between about 60° C. and about 150° C.

15. The method as defined in claim 14, wherein said temperature is about 70° C.

16. The method as defined in claim 1, wherein the sugar alcohol is stereoisomeric and wherein the stoichiometric ratio of said stereoisomeric sugar alcohol is adjusted by changing the stoichiometric ratio of said hydrogen and said sugar.

17. The method as defined in claim 1, wherein said sugar is present in said aqueous solution at a concentration between about 10 to about 70 wt.-%.

18. The method as defined in claim 17, wherein said sugar concentration is between about 15 to about 50 wt.-%.

19. The method as defined in claim 18, wherein said sugar concentration is about 40 wt.-%.

20. A method as defined in claim 1, wherein said catalytic precursor is formed by extrusion.

* * * * *